United States Patent [19]
Halbich

[11] Patent Number: 5,620,422
[45] Date of Patent: Apr. 15, 1997

[54] HYPODERMIC SYRINGE FILLING APPARATUS

[76] Inventor: Frank Halbich, W. 4595 Selway Ave., Post Falls, Id. 83854

[21] Appl. No.: 606,735

[22] Filed: Feb. 27, 1996

[51] Int. Cl.$^6$ .................................................. A61M 5/00
[52] U.S. Cl. .......................... 604/187; 604/208; 141/27
[58] Field of Search ........................... 604/187, 208–211, 604/218; 141/27, 28, 94, 95

[56] References Cited

U.S. PATENT DOCUMENTS

| | | | |
|---|---|---|---|
| 3,833,030 | 9/1974 | Waldbauer, Jr. et al. | 604/208 X |
| 3,965,945 | 6/1976 | Ross | 604/211 X |
| 4,022,207 | 5/1977 | Citrin | 604/209 |
| 4,518,387 | 5/1985 | Murphy et al. | 604/187 |
| 5,468,233 | 11/1995 | Schraga | 604/207 |

*Primary Examiner*—John D. Yasko
*Attorney, Agent, or Firm*—Wells, St. John, Roberts, Gregory & Matkin, P.S.

[57] ABSTRACT

A hypodermic syringe filling apparatus enabling filling of a hypodermic syringe with a prescribed quantity of fluid includes, a) a longitudinally elongated body having opposing longitudinal ends; b) a syringe supporting framework provided relative to the body adjacent one to the longitudinal ends, the supporting framework being sized to externally engage and retain a hypodermic syringe, the supporting framework comprising at least two upwardly open cradles, one of the cradles being sized and shaped to externally engage a cylindrical barrel portion of a hypodermic syringe received by the supporting framework, another of the cradles being sized and shaped to externally engage a syringe barrel flange of the hypodermic syringe received by the supporting framework; c) a plunger stop associated with the body and positioned to engage and stop extension of a plunger of a hypodermic syringe received by the supporting framework, the plunger stop being mounted for movement relative to the supporting framework and the body to a plurality of fixed locations to enable degree of extension of a plunger of a hypodermic syringe received by the supporting framework to be selectively varied; and d) a screw mounted for selective rotation relative to the body, the plunger stop comprising a nut, the nut threadedly engaging the screw, the nut comprising a lateral projection sized and positioned to engage an outermost head end of a plunger of a hypodermic syringe received by the supporting framework.

29 Claims, 5 Drawing Sheets

5,620,422

HYPODERMIC SYRINGE FILLING APPARATUS

TECHNICAL FIELD

This invention relates to hypodermic syringe filling devices.

BACKGROUND OF THE INVENTION

Many patients under the direction of a physician provide themselves with periodic doses of medication by hypodermic injection. Probably the most common instance of such is the insulin injections that diabetics must provide themselves with on a daily basis.

One thing key to providing such injections is to insure that the correct dose is administered with each injection. To fill the syringe, the patient typically inserts the needle of the syringe into a vial containing the desired medication. The syringe plunger is then withdrawn and stopped at a location relative to gradation markings on the outside of the syringe to assure that a proper quantity of medication liquid is withdrawn into the syringe barrel. Such a procedure can however be difficult or impossible for the blind or other visually impaired people.

One technique to overcome such drawback would be for the pharmacist to provide the patient with pre-filled syringes having the desired quantity of medication provided therein. This would undesirably however require that the manufacturer provide various syringes filled with various medications at selected dosages, or require the pharmacist to fill a series of syringes for the patients with the correct medication and dosages. Neither of these alternatives is very desirable. In the first, considerable expense would be associated with the manufacturer providing a plurality of syringes with various medication at various dosages. Having a pharmacist provide the filled syringes would breach the sterile field of the syringes, subjecting the patient to greater risk of infection.

Accordingly, a need remains to assist the visually impaired and other people to, in a more automated way, provide filling of a syringe with the desired mediation to a predetermined dosage.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the invention, a hypodermic syringe filling apparatus enabling filling of a hypodermic syringe with a prescribed quantity of fluid comprises:

a body;

a syringe supporting framework provided relative to the body and being sized to externally engage and retain a hypodermic syringe; and a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied.

In accordance with another aspect of the invention, a hypodermic syringe filling apparatus enabling filling of a hypodermic syringe with a prescribed quantity of fluid comprises:

a longitudinally elongated body having opposing longitudinal ends;

a syringe supporting framework provided relative to the body adjacent one to the longitudinal ends, the supporting framework being sized to externally engage and retain a hypodermic syringe, the supporting framework comprising at least two upwardly open cradles, one of the cradles being sized and shaped to externally engage a cylindrical barrel portion of a hypodermic syringe received by the supporting framework, another of the cradles being sized and shaped to externally engage a syringe barrel flange of the hypodermic syringe received by the supporting framework; and a plunger stop associated with the body and positioned to engage and stop extension of a plunger of a hypodermic syringe received by the supporting framework, the plunger stop being mounted for movement relative to the supporting framework and the body to a plurality of fixed locations to enable degree of extension of a plunger of a hypodermic syringe received by the supporting framework to be selectively varied.

In accordance with still another aspect of the invention, a hypodermic syringe filling apparatus enabling filling of a hypodermic syringe with a prescribed quantity of fluid comprises:

a longitudinally elongated body;

a syringe supporting framework provided relative to the body and being sized to externally engage and retain a hypodermic syringe;

a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied; and a screw mounted for selective rotation relative to the body, the plunger stop comprising a nut, the nut threadedly engaging the screw, the nut comprising a lateral projection sized and positioned to engage an outermost head end of a plunger of a hypodermic syringe received by the supporting framework.

Referring initially to FIGS. 1–7, a hypodermic syringe filling apparatus enabling filling of a hypodermic syringe with the prescribed quantity of fluid is indicated generally with reference numeral 10. Such comprises a longitudinally elongated body 12 configured for retaining a hypodermic syringe 14. For purposes of the continuing discussion, the illustrated example syringe 14 comprises a cylindrical barrel portion 15, a syringe finger flange 16 having opposing flange ears 17, a plunger 18 slidably received within barrel 15, and a plunger head/end 19.

A syringe supporting framework 20 is provided relative to body 12 and is sized to externally engage and retain hypodermic syringe 14. A plunger stop 22 is associated with body 12 and positioned to engage and stop extension of plunger 18 of syringe 14 received by supporting framework 20. Plunger stop 22 is mounted for movement relative to supporting framework 20 to a plurality of fixed locations to enable degree of extension of plunger 18 to be selectively varied.

More specifically, elongated body 12 has opposing longitudinal ends 24 and 26. Syringe supporting framework 20 is provided at or adjacent longitudinal end 26. Body 12 comprises a pair of juxtaposed pieces in the form of an upper portion 28 and a lower portion 30 which are retained together by a series of three screws 31. Supporting framework 20 is formed at a fore portion of upper component 28.

Supporting framework 20 comprises three upwardly open cradles 32, 33 and 34. Cradle 32 is sized and shaped to externally engage cylindrical barrel portion 15 of hypodermic syringe 14. Cradles 33 and 34 are sized and shaped to externally engage flange ears 17 of syringe barrel flange 16. Cradle 32 includes a pair of lower projecting pinch arms 36. A user can inwardly press arms 36 in the direction of each other to cause wider opening of the upper portion of cradle 32 for ease in inserting syringe barrel 15 therein. Cradles 33 and 34 are preferably sized to more loosely receive flange ears Body halves 28 and 30 internally receive a screw 40 for selective rotation relative to body 12. Screw 40 comprises opposing longitudinal ends 44 and 46 which are not threaded. Longitudinal end 44 is provided with a slot 45 configured for receiving a flat head screw driver. Slot 45 is accessible from longitudinal end 24 of body 12. Body halves 28 anti 30 comprise two opposing pairs 41 and 42 of cooperating journal recesses which rotatably receive longitudinal ends 44 and 46 of screw 40. Recesses 41 rotatably receive longitudinal end 44 of screw 40, while recesses 42 rotatably receive longitudinal end 46 of screw 40.

Figure 1:
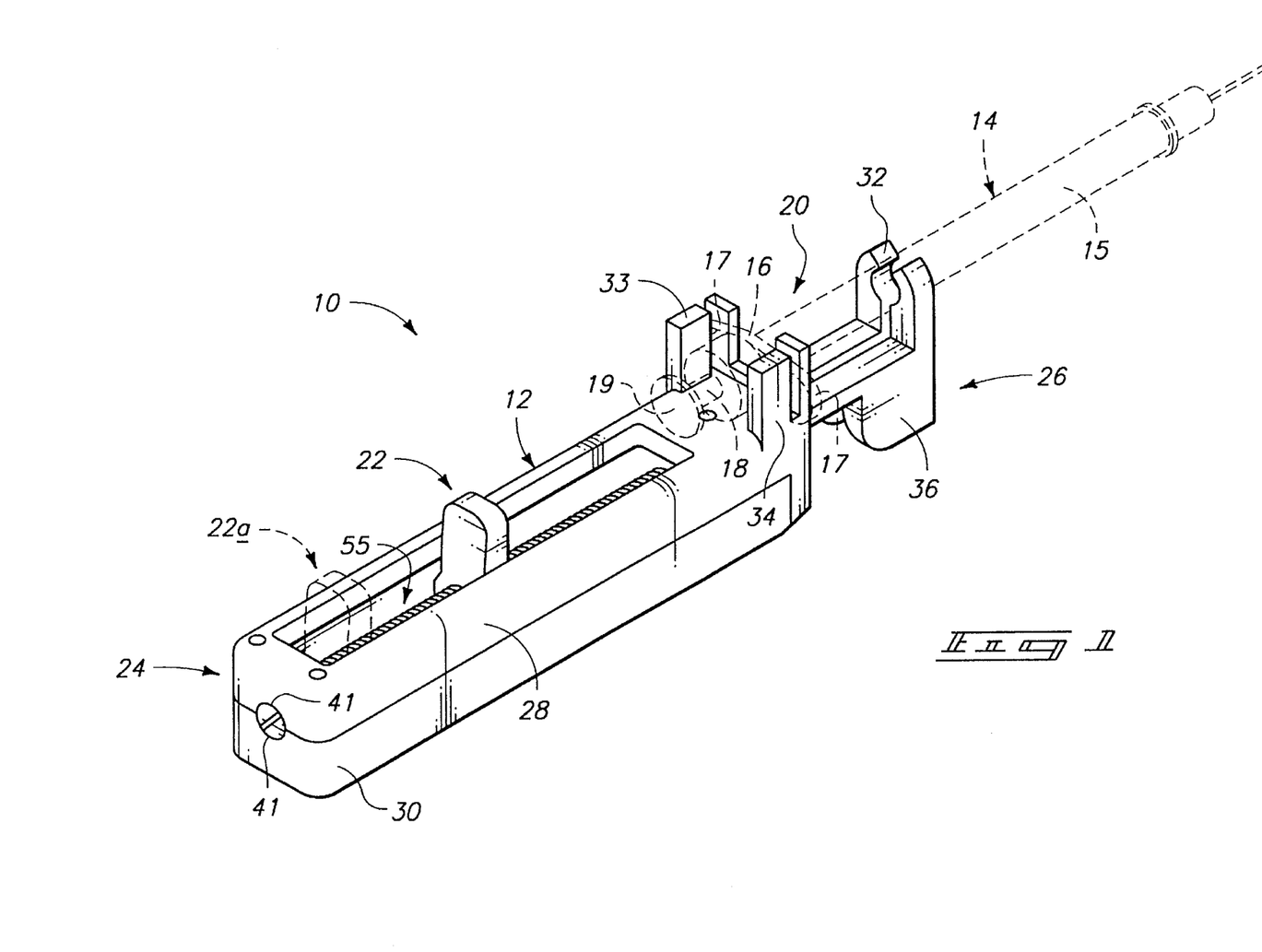
FIG. 1 is a perspective view of a hypodermic syringe filling apparatus in accordance with the invention.
Figure 2:
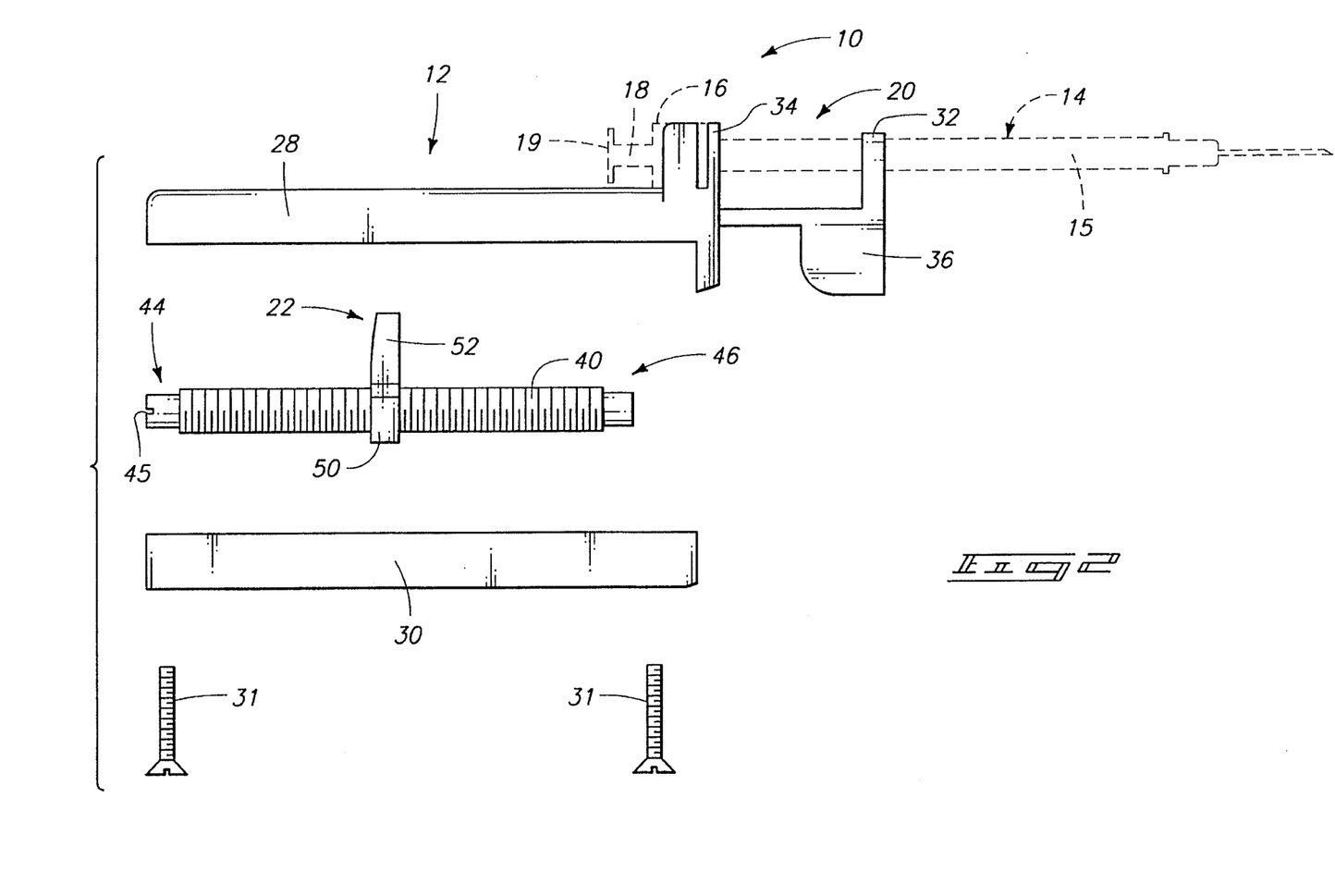
FIG. 2 is an exploded view of the FIG. 1 syringe filling apparatus.
Figure 3:
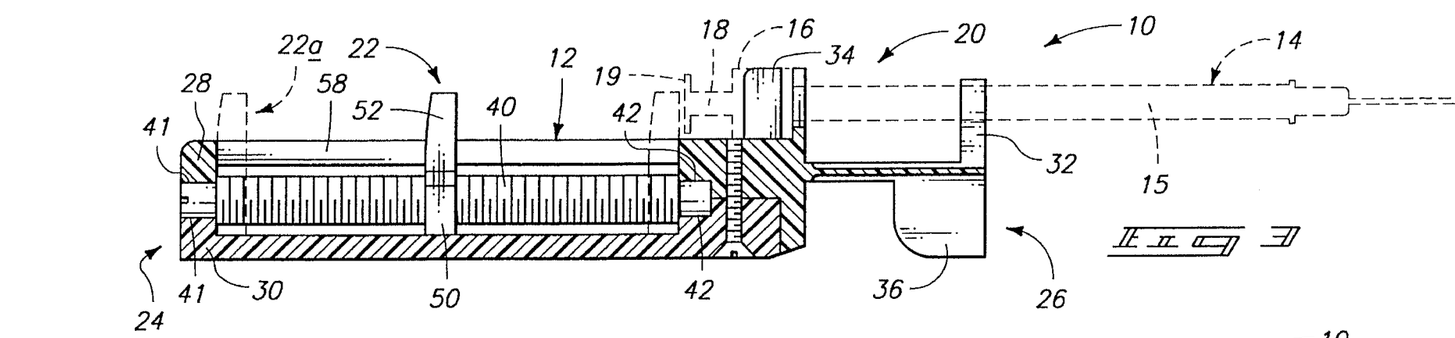
FIG. 3 is a longitudinal sectional view of the FIG. 1 syringe filling apparatus.
Figure 4:
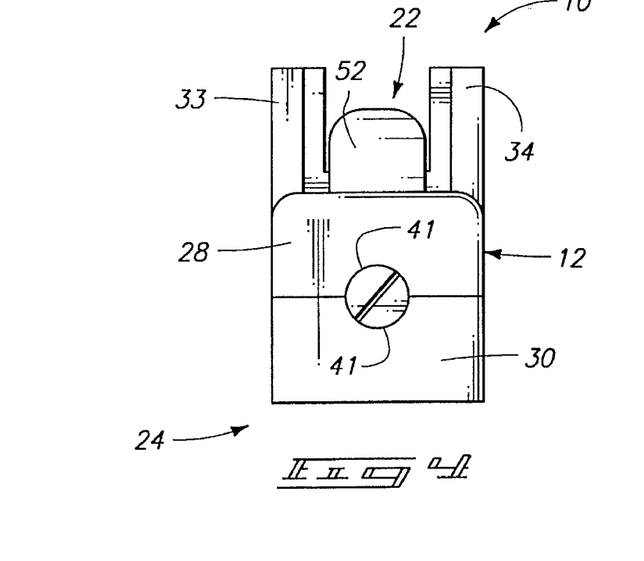
FIG. 4 is a rear end view of the FIG. 1 syringe filling apparatus.
Figure 5:
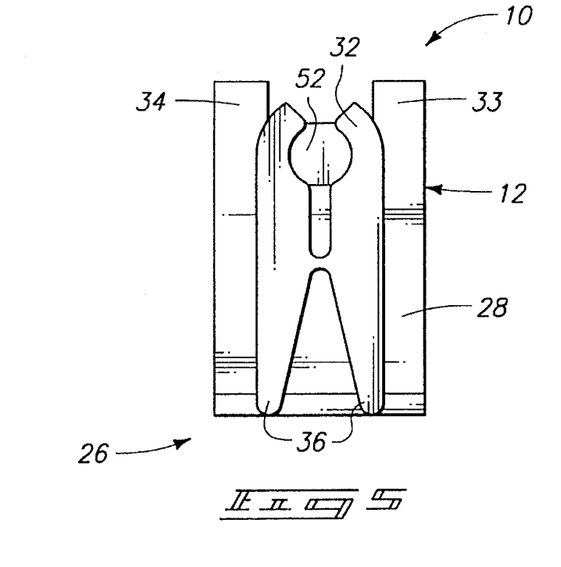
FIG. 5 is a front end view of the FIG. 1 syringe filling apparatus.
Figure 6:
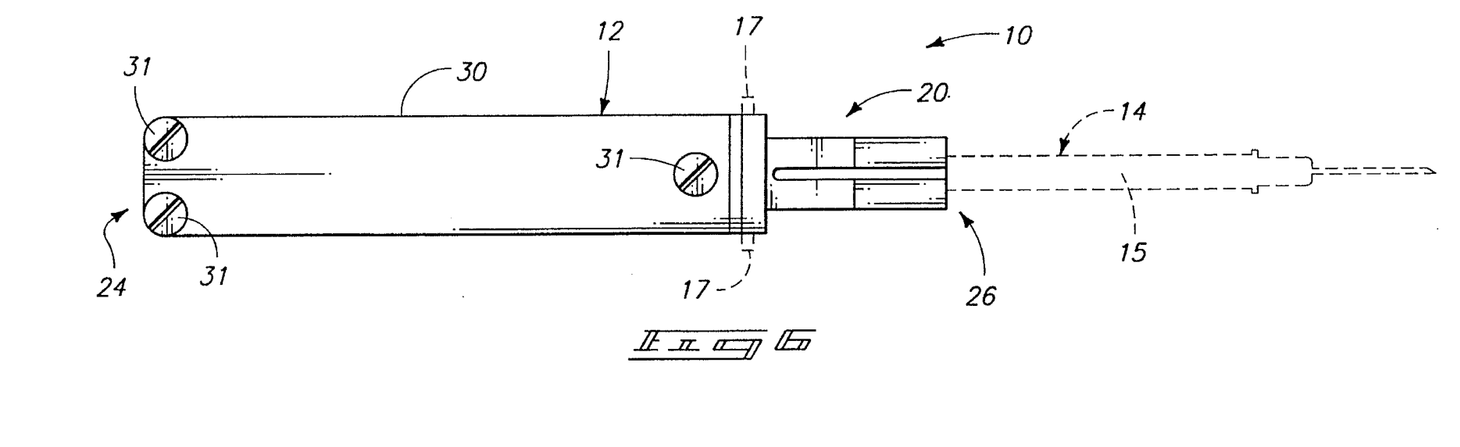
FIG. 6 is a bottom longitudinal view of the FIG. 1 syringe filling apparatus.
Figure 7:
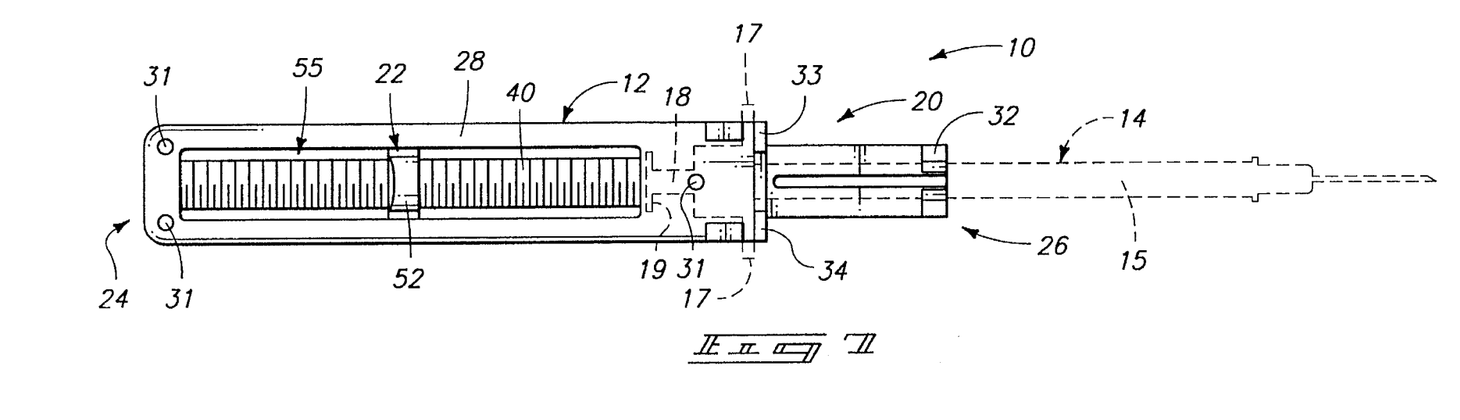
FIG. 7 is a top longitudinal view of the FIG. 1 syringe filling apparatus.

Plunger stop 22 comprises a nut 50 which is threadedly engaged relative to screw 40. Nut 50 includes a lateral projection 52 sized and positioned to engage outermost head/end 19 of syringe plunger 18 received relative to supporting framework 20. Upper body portion 28, and thereby body 12, includes an elongated slot 55 within or through which lateral projection 52 extends and moves upon rotation of screw 40. For example, FIG. 1 illustrates an alternate adjusted plunger position 22a in phantom which can be achieved by proper rotation of screw 40.

Figure 8:
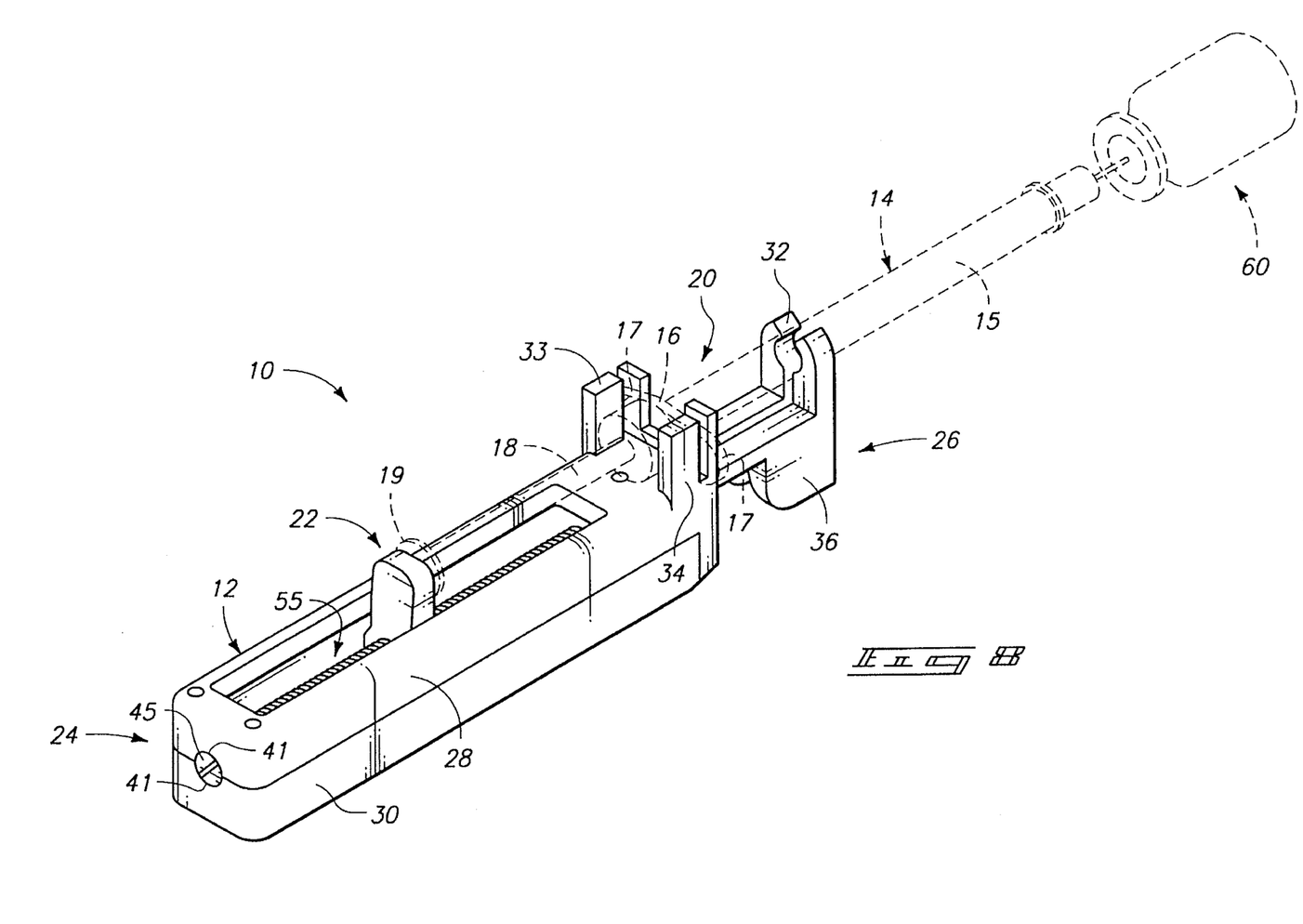
FIG. 8 is another perspective view of the FIG. 1 syringe filling apparatus shown with a plunger of a hypodermic syringe received by the apparatus in a fully extended position relative to the illustrated adjustment of the apparatus.

In operation, for a visually impaired person for example, typically another person or care giver such a physician or nurse would adjust apparatus 10 such that plunger stop 22 is positioned at a desired location for desired precise quantity filling of a syringe 14 received by the apparatus. For example, FIG. 8 illustrates a vial 60 engaged relative to hypodermic syringe 14 received by apparatus 10. The person providing the rejection would extend plunger 18 from hypodermic syringe 14 to the point where plunger head 19 firmly abuts lateral projection 52 of plunger stop 22. With plunger stop 22 having been pre-set relative to desired filling of a predetermined size or configured syringe 14, the desired dosage filling of the syringe is assured. Screw 40 is preferably provided in an example manner as shown to both enable easy subsequent adjustment by a care giver, but not so exposed to result in inadvertent adjustment by the patient which would adversely effect otherwise precise enabled positioning of plunger stop 22. The preferred material of construction for screws 31 is stainless steel, with the various other illustrated components preferably comprising any suitable plastic.

The above-described preferred embodiments pertain to an experimental prototype of the invention. It is expected that other preferred embodiments of the invention will comprise other mechanisms for interconnecting the body halves 28 and 30, instead of, or in addition to, the screws 31. For instance, the upper portion 28 and the lower portion 30 may be interconnected by a weld, such as would be formed by a sonic welding process.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A hypodermic syringe filling apparatus enabling filling of a hypodermic syringe with a prescribed quantity of fluid, the filling apparatus comprising:

a body comprising a pair of juxtaposed portions mounted to one another, the juxtaposed portions comprising two opposing pairs of journal recesses which together form two opposing journals within the body;

a screw mounted for selective rotation relative to the body, the screw having opposing longitudinal ends which are rotatably received within the opposing journals within the body;

a syringe supporting framework provided relative to the body and being sized to externally engage and retain a hypodermic syringe; and a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied, the plunger stop threadedly engaging the screw.

2. The hypodermic syringe filling apparatus of claim 1 wherein the plunger stop is mounted for movement relative to the body.

3. The hypodermic syringe filling apparatus of claim 1 wherein the body is longitudinally elongated.

4. The hypodermic syringe filling apparatus of claim 1 wherein the body is longitudinally elongated and has opposing longitudinal ends, the supporting framework being provided adjacent one of the opposing ends.

5. The hypodermic syringe filling apparatus of claim 1 wherein the supporting framework comprises at least one upwardly open cradle sized to externally engage and retain a hypodermic syringe.

6. The hypodermic syringe filling apparatus of claim 1 wherein the supporting framework comprises at least two upwardly open cradles sized to externally engage and retain a hypodermic syringe.

7. The hypodermic syringe filling apparatus of claim 1 wherein the supporting framework is sized and shaped to externally engage a syringe barrel flange of a hypodermic syringe received by the supporting framework.

8. The hypodermic syringe filling apparatus of claim 1 wherein the supporting framework is sized and shaped to externally engage a cylindrical barrel portion of a hypodermic syringe received by the supporting framework.

9. The hypodermic syringe filling apparatus of claim 1 wherein the supporting framework is sized and shaped to externally engage both, a) a syringe barrel flange, and b) a cylindrical barrel portion, of a hypodermic syringe received by the supporting framework.

10. The hypodermic syringe filling apparatus of claim 1 wherein, the supporting framework comprises at least two upwardly open cradles, one of the cradles being sized and shaped to externally engage a cylindrical barrel portion of a hypodermic syringe received by the supporting framework, another of the cradles being sized and shaped to externally engage a syringe barrel flange of the hypodermic syringe received by the supporting framework.

11. The hypodermic syringe filling apparatus of claim 1 wherein the plunger stop threadedly engages the screw through a nut, the nut comprising a lateral projection sized and positioned to engage an outermost head end of a plunger of a hypodermic syringe received by the supporting framework.

12. The hypodermic syringe filling apparatus of claim 1 further comprising a screw mounted for selective rotation relative to the body, the plunger stop comprising a nut, the nut threadedly engaging the screw, the nut comprising a lateral projection sized and positioned to engage an outermost head end of a plunger of a hypodermic syringe received by the supporting framework, the body including an elongated open slot within which the lateral projection moves upon rotation of the screw.

13. The hypodermic syringe filling apparatus of claim 1 wherein the plunger stop threadedly engages the screw through a nut, the nut comprising a lateral projection sized and positioned to engage an outermost head end of a plunger of a hypodermic syringe received by the supporting framework, the body including an elongated open slot within which the lateral projection moves upon rotation of the screw.

14. A hypodermic syringe filling apparatus enabling filling of a hypodermic syringe with a prescribed quantity of fluid, the filling apparatus comprising:

a longitudinally elongated body having opposing longitudinal ends, the body comprising a pair of juxtaposed portions mounted to one another, the juxtaposed portions comprising two opposing pairs of journal recesses which together form two opposing journals within the body;

a screw mounted for selective rotation relative to the body, the screw having opposing longitudinal ends which are rotatably received within the opposing journals within the body;

a syringe supporting framework provided relative to the body adjacent one of the longitudinal ends, the supporting framework being sized to externally engage and retain a hypodermic syringe, the supporting framework comprising at least two upwardly open cradles, a first of the at least two cradles being sized and shaped to externally engage a cylindrical barrel portion of a hypodermic syringe received by the supporting framework, a second of the at least two cradles being sized and shaped to externally engage a syringe barrel flange of the hypodermic syringe received by the supporting framework; and a plunger stop associated with the body and positioned to engage and stop extension of a plunger of a hypodermic syringe received by the supporting framework, the plunger stop being mounted for movement relative to the supporting framework and the body to a plurality of fixed locations to enable degree of extension of a plunger of a hypodermic syringe received by the supporting framework to be selectively varied, the plunger stop threadedly engaging the screw.

15. The hypodermic syringe filling apparatus of claim 14 wherein the plunger stop is threadedly engaged to the screw through a nut, the nut comprising a lateral projection sized and positioned to engage an outermost head end of a plunger of a hypodermic syringe received by the supporting framework.

16. The hypodermic syringe filling apparatus of claim 14 wherein the plunger stop is threadedly engaged to the screw through a nut, the nut comprising a lateral projection sized and positioned to engage an outermost head end of a plunger of a hypodermic syringe received by the supporting framework, the body including an elongated open slot within which the lateral projection moves upon rotation of the screw.

17. A hypodermic syringe filling apparatus enabling filling of a hypodermic syringe with a prescribed quantity of fluid, the filling apparatus comprising:

a longitudinally elongated body, the body comprising a pair of juxtaposed portions mounted to one another, the juxtaposed portions comprising two opposing pairs of journal recesses which together form two opposing journals within the body;

a syringe supporting framework provided relative to the body and being sized to externally engage and retain a hypodermic syringe;

a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied; and a screw mounted for selective rotation relative to the body, the screw having opposing longitudinal ends which are rotatably received within the opposing journals within the body, the plunger stop comprising a nut, the nut threadedly engaging the screw, the nut comprising a lateral projection sized and positioned to engage an outermost head end of a plunger of a hypodermic syringe received by the supporting framework.

18. The hypodermic syringe filling apparatus of claim 17 wherein the supporting framework comprises at least one upwardly open cradle sized to externally engage and retain a hypodermic syringe.

19. The hypodermic syringe filling apparatus of claim 17 wherein the supporting framework comprises at least two upwardly open cradles sized to externally engage and retain a hypodermic syringe.

20. The hypodermic syringe filling apparatus of claim 17 wherein the supporting framework is sized and shaped to externally engage a syringe barrel flange of a hypodermic syringe received by the supporting framework.

21. The hypodermic syringe filling apparatus of claim 17 wherein the supporting framework comprises at least two upwardly open cradles, one of the cradles being sized and shaped to externally engage a cylindrical barrel portion of a hypodermic syringe received by the supporting framework, another of the cradles being sized and shaped to externally engage a syringe barrel flange of the hypodermic syringe received by the supporting framework.

22. The hypodermic syringe filling apparatus of claim 17 wherein the body includes an elongated open slot within which the lateral projection moves upon rotation of the screw.

23. A hypodermic syringe filling apparatus enabling filling of a hypodermic syringe with a prescribed quantity of fluid, the filling apparatus comprising:

a longitudinally elongated body having opposing longitudinal ends;

a syringe supporting framework provided adjacent to one of the longitudinal ends of the body, the framework being sized to externally engage and retain a hypodermic syringe, the supporting framework comprising at least three upwardly open cradles, one of the cradles being sized and shaped to externally engage a cylindrical barrel portion of a hypodermic syringe received by the supporting framework, two of the cradles being sized and shaped to externally engage a syringe barrel flange of a hypodermic syringe received by the supporting framework;

a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied; and a screw mounted for selective rotation relative to the body, the plunger stop threadedly engaging the screw, the screw having opposing longitudinal ends, the body comprising a pair of juxtaposed portions mounted to one another, the juxtaposed portions comprising two opposing pairs of journal recesses which rotatably receive the respective opposing longitudinal ends of the screw, the plunger stop comprising a nut, the nut threadedly engaging the screw, the nut comprising a lateral projection sized and positioned to engage an outermost head end of a plunger of a hypodermic syringe received by the supporting framework, the body including an elongated open slot within which the lateral projection moves upon rotation of the screw.

24. The apparatus of claim 1 further comprising a syringe supporting framework adjacent the body, the supporting framework comprising a cradle for holding a syringe and a pair of lower projecting pinch arms attached to the cradle and configured for inward movement toward one another, the lower projecting pinch arms and cradle being together configured to couple inward movement of the pinch arms to widening of an opening of the cradle.

25. The apparatus of claim 14 wherein the supporting framework further comprises a pair of lower projecting pinch arms attached to the first cradle and configured for inward movement toward one another, the lower projecting pinch arms and the first cradle being together configured to couple inward movement of the pinch arms to widening of the upward opening of the first cradle.

26. The apparatus of claim 17 wherein the supporting framework comprises an upwardly open cradle for holding a syringe and a pair of lower projecting pinch arms attached to the cradle and configured for inward movement toward one another, the lower projecting pinch arms and cradle being together configured to couple inward movement of the pinch arms to widening of an opening of the cradle.

27. A hypodermic syringe filling apparatus enabling filling of a hypodermic syringe with a prescribed quantity of fluid, the filling apparatus comprising:

a longitudinally elongated body having opposing longitudinal ends;

a syringe supporting framework provided adjacent to one of the longitudinal ends of the body, the framework being sized to externally engage and retain a hypodermic syringe, the supporting framework comprising at least three upwardly open cradles, a first of the cradles being sized and shaped to externally engage a cylindrical barrel portion of a hypodermic syringe received by the supporting framework, a second and a third of the cradles being sized and shaped to externally engage a syringe barrel flange of a hypodermic syringe received by the supporting framework, the supporting framework further comprising a pair of lower projecting pinch arms attached to the first cradle, the pinch arms being configured for inward movement toward one another, the pinch arms and the first cradle being together configured to couple inward movement of the pinch arms to widening of the upward opening of the first cradle;

a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied; and a screw mounted for selective rotation relative to the body, the plunger stop threadedly engaging the screw, the screw having opposing longitudinal ends, the body comprising a pair of juxtaposed portions mounted to one another, the juxtaposed portions comprising two opposing pairs of journal recesses which rotatably receive the respective opposing longitudinal ends of the screw, the plunger stop comprising a nut, the nut threadedly engaging the screw, the nut comprising a lateral projection sized and positioned to engage an outermost head end of a plunger of a hypodermic syringe received by the supporting framework, the body including an elongated open slot within which the lateral projection moves upon rotation of the screw.

28. A hypodermic syringe filling apparatus enabling filling of a hypodermic syringe with a prescribed quantity of fluid, the filling apparatus comprising:

a longitudinally elongated body having opposing longitudinal ends; and a syringe supporting framework provided adjacent to one of the longitudinal ends of the body, the framework being sized to externally engage and retain a hypodermic syringe, the supporting framework comprising at least three upwardly open cradles, a first of the cradles being sized and shaped to externally engage a cylindrical barrel portion of a hypodermic syringe received by the supporting framework, a second and a third of the cradles being sized and shaped to externally engage a syringe barrel flange of a hypodermic syringe received by the supporting framework, the supporting framework further comprising a pair of lower projecting pinch arms attached to the first cradle, the pinch arms being configured for inward movement toward one another, the pinch arms and the first cradle being together configured to couple inward movement of the pinch arms to widening of the upward opening of the first cradle.

29. A hypodermic syringe filling apparatus enabling filling of a hypodermic syringe with a prescribed quantity of fluid, the filling apparatus comprising:

a body; and a syringe supporting framework provided joined to the body, the framework being sized to externally engage and retain a hypodermic syringe, the supporting framework comprising a cradle sized and shaped to engage a barrel portion of a hypodermic syringe, the supporting framework further comprising a pair of lower projecting pinch arms attached to the cradle, the pinch arms being configured for inward movement toward one another, the pinch arms and the cradle being together configured to couple inward movement of the pinch arms to widening of an opening of the cradle.

* * * * *